(12) United States Patent
Phelan et al.

(10) Patent No.: US 7,315,378 B2
(45) Date of Patent: Jan. 1, 2008

(54) OPTICAL ARRANGEMENT FOR ASSAY READING DEVICE

(75) Inventors: Andrew Peter Phelan, Bedford (GB); Stephen Paul Sharrock, Bedford (GB)

(73) Assignee: Inverness Medical Switzerland GmbH, Zug (CH)

( * ) Notice: Subject to any disclaimer, the term of this patent is extended or adjusted under 35 U.S.C. 154(b) by 0 days.

(21) Appl. No.: 10/816,216

(22) Filed: Apr. 1, 2004

(65) Prior Publication Data

US 2005/0036148 A1    Feb. 17, 2005

Related U.S. Application Data

(60) Provisional application No. 60/508,001, filed on Oct. 2, 2003.

(30) Foreign Application Priority Data

Jun. 4, 2003    (GB) ................... 0312802.2

(51) Int. Cl.
*G01N 21/00*    (2006.01)
(52) U.S. Cl. ........................ 356/436; 356/39
(58) Field of Classification Search ............... 356/436, 356/39, 446, 433, 448, 27
See application file for complete search history.

(56) References Cited

U.S. PATENT DOCUMENTS

| | | |
|---|---|---|
| 3,941,477 A | 3/1976 | Schodl et al. |
| 4,399,362 A | 8/1983 | Cormier et al. |
| 4,420,566 A | 12/1983 | Jessop et al. |
| 4,523,853 A | 6/1985 | Rosenbladt et al. ........ 356/446 |
| 4,676,653 A * | 6/1987 | Strohmeier et al. ......... 356/446 |
| 4,995,402 A | 2/1991 | Smith et al. |
| 5,049,487 A | 9/1991 | Phillips et al. |
| 5,114,350 A | 5/1992 | Hewett |
| 5,145,789 A | 9/1992 | Corti et al. |

(Continued)

FOREIGN PATENT DOCUMENTS

DE    19628562    1/1998

(Continued)

OTHER PUBLICATIONS

Search Report for GB 0312802.2, Date of Search Dec. 1, 2003.

(Continued)

*Primary Examiner*—Gregory J. Toatley, Jr.
*Assistant Examiner*—Kara Geisel
(74) *Attorney, Agent, or Firm*—Scott E. Kamholz; Foley Hoag LLP (57) ABSTRACT

Disclosed, in one aspect, is an assay result reading device for reading the result of an assay performed using a test strip, the device comprising: a light source or sources, said light source/s emitting light incident upon at least two, spatially separated zones of the test strip; and a photodetector which detects light emanating from each of the two said zones; in a further aspect is disclosed an assay result reading device for reading the result of an assay performed using a test strip, the device comprising: at least one light source incident upon a zone of the test strip; and at least two photodetectors both of which are able to detect some of the light emanating from the zone of the test strip illuminated by the light source.

34 Claims, 7 Drawing Sheets

U.S. PATENT DOCUMENTS

| | | | |
|---|---|---|---|
| 5,304,468 A | 4/1994 | Phillips et al. | 435/14 |
| 5,344,754 A | 9/1994 | Zweig | |
| 5,504,013 A | 4/1996 | Senior | 436/165 |
| 5,580,794 A | 12/1996 | Allen | 436/169 |
| 5,679,584 A | 10/1997 | Mileaf et al. | |
| 5,786,220 A | 7/1998 | Pronovost et al. | |
| 5,837,546 A | 11/1998 | Allen et al. | |
| 5,885,839 A | 3/1999 | Lingane et al. | |
| 5,889,585 A * | 3/1999 | Markart | 356/39 |
| 5,968,835 A | 10/1999 | Aoki et al. | 436/110 |
| 5,968,839 A | 10/1999 | Blatt et al. | 436/513 |
| 6,055,060 A * | 4/2000 | Bolduan et al. | 356/433 |
| 6,156,271 A | 12/2000 | May | 422/58 |
| 6,194,222 B1 | 2/2001 | Buechler et al. | 436/518 |
| 6,235,241 B1 | 5/2001 | Catt et al. | 422/56 |
| 6,361,956 B1 | 3/2002 | Hanninen et al. | |
| 6,399,398 B1 | 6/2002 | Cunningham et al. | 436/534 |
| 6,448,067 B1 * | 9/2002 | Tajnafoi | 435/288.7 |
| 6,454,726 B1 | 9/2002 | Catt et al. | |
| 6,707,554 B1 | 3/2004 | Miltner et al. | 356/433 |
| 6,825,918 B2 * | 11/2004 | Eisenmann et al. | 356/39 |
| 6,949,221 B2 | 9/2005 | Kiser et al. | |
| 6,951,631 B1 | 10/2005 | Catt et al. | 422/56 |
| 7,018,847 B2 | 3/2006 | Mendel-Hartvig et al. | |
| 2002/0192833 A1 * | 12/2002 | Pan et al. | 436/164 |
| 2003/0180815 A1 | 9/2003 | Rawson et al. | |
| 2004/0152208 A1 | 8/2004 | Hutchinson | |
| 2004/0152209 A1 | 8/2004 | Zin et al. | |

FOREIGN PATENT DOCUMENTS

| | | |
|---|---|---|
| EP | 0291194 B1 | 2/1994 |
| EP | 0728309 B1 | 8/1997 |
| EP | 0819943 A2 | 1/1998 |
| EP | 0 826 777 A1 | 3/1998 |
| EP | 0833145 B1 | 4/1998 |
| EP | 0782707 B1 | 11/1998 |
| EP | 0653625 B1 | 9/2002 |
| EP | 0291194 B2 | 7/2003 |
| EP | 0291194 B8 | 10/2003 |
| GB | 2365526 | 7/2000 |
| WO | WO 1998/025143 A1 | 6/1998 |
| WO | O1999/35602 | 7/1999 |
| WO | WO 00/19185 A1 | 4/2000 |
| WO | O2004/070353 | 8/2004 |

OTHER PUBLICATIONS

Search Report dated Dec. 1, 2003 for GB 0312815.4.
European Search Report dated Jul. 3 2006 for EP 04 25 3076.
Search Report dated Jul. 3 for FR 0406067.
Search Report dated Dec. 1, 2003 for GB0312801.4.
European Search Report dated Jul. 11, 2006 for EP 04 25 3077.
Search Report dated Jul. 11, 2006 for FR 0406065.
Search Report dated Dec. 1, 2003 for GB 0312802.2.
European Search Report dated Jul. 14, 2006 for EP 04 2503078.
Search Report dated Jul. 14, 2006 for FR0406066.

* cited by examiner

OPTICAL ARRANGEMENT FOR ASSAY READING DEVICE

CROSS-REFERENCE TO RELATED APPLICATION

This application claims the benefit of U.S. Provisional Patent Application Ser. No. 60/508,001, filed Oct. 2, 2003, the entire contents of which are hereby incorporated herein by this reference.

FIELD

The disclosed subject matter relates to assay reading devices for the measurement of analytes. In particular it relates to electronic readers for use with assay test-strips which use optical methods of measurement.

INTRODUCTION

Disposable analytical devices suitable for home testing of analytes are now widely commercially available. A lateral flow immunoassay device suitable for this purpose for the measurement of the pregnancy hormone human chorionic gonadotropin (hCG) is sold by Unipath under the brand-name CLEARBLUE® and is disclosed in EP291194.

EP291194 discloses an immunoassay device comprising a porous carrier containing a particulate labelled specific binding reagent for an analyte, which reagent is freely mobile when in the moist state, and an unlabelled specific binding reagent for the same analyte, which reagent is immobilised in a detection zone or test zone downstream from the unlabelled specific binding reagent. Liquid sample suspected of containing analyte is applied to the porous carrier whereupon it interacts with the particulate labelled binding reagent to form an analyte-binding partner complex. The particulate label is coloured and is typically gold or a dyed polymer, for example latex or polyurethane. The complex thereafter migrates into a detection zone whereupon it forms a further complex with the immobilised unlabelled specific binding reagent enabling the extent of analyte present to be observed.

However such commercially available devices as disclosed above require the result to be interpreted by the user. This introduces a degree of subjectivity, which is undesirable.

Electronic readers for use in combination with assay test-strips for determining the concentration and/or amount of analyte in a fluid sample are known. EP653625 discloses such a device which uses an optical method in order to determine the result. An assay test strip such as that disclosed in EP291194 is inserted into a reader such that the strip is aligned with optics present within the reader. Light from a light source, such as a light emitting diode (LED), is shone onto the test strip and either reflected or transmitted light is detected by a photodetector. Typically, the reader will have more than one LED, and a corresponding photodetector is provided for each of the plurality of LED's.

U.S. Pat. No. 5,580,794 discloses a fully disposable integrated assay reader and lateral flow assay test strip whereby optics present in the reader enable the result to be determined optically using reflectance measurements.

An important consideration in assay reading devices of this type is the requirement that the assay reader and the test strip are carefully aligned. This is because the visible signal formed in the detection zone (and the control zone, if present) is fairly narrow (about 1 mm wide), so a small displacement of the detection or control zone relative to the respective photodetector may significantly affect the reading made by the photodetector. In addition, it is generally important that the photodetector is as close as possible to the test strip, because the amount of light which is 'captured' by the photodiode is fairly small, and the signal intensity normally obeys the inverse square law, so that it diminishes rapidly as the separation between the test strip and the photodetector increases. Thus there is a requirement for the user to carefully align the test stick with the assay result reader which, especially for devices intended to be used in the home, can be problematic.

One solution to this problem is provided by U.S. Pat. No. 5,580,794, wherein the assay strip is provided as an integral component of the result reader, thereby avoiding the need for the user to insert the test strip into the reader. An alternative solution is taught by EP 0833145, which discloses a test strip and assay result reader combination, wherein the assay result reading device can be successfully triggered to make a reading only when there is a precise three-dimensional fit between the test strip and the reader, thereby ensuring the correct alignment has been obtained.

SUMMARY

The present disclosure provides inexpensive, typically disposable, assay readers either for use with, or in integral combination with, an assay test strip such as disclosed by EP291194. The optics are provided in a compact arrangement well-suited, for example, for a handheld device. The arrangement also provides an optimal or near optimal path length between the light source and photodetector thus establishing a strong signal.

In some embodiments, an assay result reading device for reading the result of an assay performed using a test strip includes a light source capable of emitting light incident upon at least two spatially separated zones of the test strip, and a photodetector which detects light emanating from each of the two said zones. A photodetector which is used to detect light emanating from two distinct zones of the test strip, may be referred to as a "shared" photodetector.

In some embodiments, an assay result reading device for reading the result of an assay performed using a test strip includes a light source capable of emitting light incident upon a zone of the test strip, and two photodetectors both of which are able to detect some of the light emanating from the zone of the test strip illuminated by the light source. Such a zone, "read" by two or more photodetectors, may be referred to as a "commonly read" zone.

In other embodiments, the invention provides methods of reading the result of an assay performed using a test strip in accordance with the embodiments described above.

DETAILED DESCRIPTION

The optical arrangements for assay readers described herein promote simplicity and economy. The manufacturing cost of the device is an especially important consideration if the reader is intended to be disposable; the photodetectors themselves, being relatively expensive components, form a significant part of the overall cost.

A further advantage is that the arrangement can provide greater accuracy and reduce the need for accurate positioning of the test strip relative to the reader. Suppose, for example, a test strip were provided with two separate, but closely spaced, control zones and a photodetector were positioned in the reader so as to be between the two control zones. If the test strip were slightly misaligned, laterally, relative to the assay reader device, the signal from one of the control zones would be less intense as the zone in question would be further from the photodetector. However, the other control zone would necessarily be closer to the photodetector by a corresponding amount, and would therefore provide a stronger signal to compensate for the weaker signal from the other zone. Furthermore it has been observed that the amount of bound material present at a particular zone will vary along the length of the zone in the direction of liquid flow. Preferential binding of the analyte takes place at the leading boundary edge and diminishes along the length of the zone in the direction of liquid flow. Thus any misalignment may result in a greater error than might have been expected if the analyte were captured in a uniform fashion. U.S. Pat. No. 5,968,839 discloses an electronic assay reader for use with a test strip, wherein it is attempted to compensate for this non-uniform binding by the provision in the relevant binding zone of a plurality of deposits of immobilised capture reagent, the density of which deposits increases from the leading boundary to the trailing edge of the zone.

Similarly, some of the arrangements described herein also reduce the requirement for precise relative positioning of the test strip and the assay result reading device: there is an in-built signal compensation for any misalignment between the test strip and the assay result reader for any zone which is commonly read by the two or more photodetectors, because relative movement of the commonly read zone away from one of the photodetectors will necessarily (within certain limits) involve movement by a corresponding amount towards the other photodetector/s.

The light emanating from the zone or zones, as appropriate, may be light which is reflected from the test strip or, in the case of a test strip which is transparent or translucent (especially when wet e.g. following the application of a liquid sample), light which is transmitted through the test strip. For the purposes of the present specification, light incident upon a particular zone of a test strip from a light source, and reflected by the strip or transmitted therethrough, may be regarded as "emanating" from the strip, although of course the light actually originates from the light source.

The preferred light sources are light emitting diodes (LED's), and the preferred photodetector is a photodiode.

Reflected light and/or transmitted light may be measured by the photodetector. For the present purposes, reflected light is taken to mean that light from the light source is reflected from the test strip onto the photodetector. In this situation, the detector is typically provided on the same side of the test strip as the light source. Transmitted light refers to light that passes through the test strip and typically the detector is provided on the opposite side of the test strip to the light source. For the purposes of a reflectance measurement, the test strip may be provided with a backing such as a white reflective MYLAR® plastic layer. Thus light from the light source will fall upon the test strip, some will be reflected from its surface and some will penetrate into the test strip and be reflected at any depth up to and including the depth at which the reflective layer is provided. Thus, a reflectance type of measurement may actually involve transmission of light through at least some of the thickness of the test strip. Generally, measurement of reflected light is preferred.

It is especially preferred that the reading device of the second aspect comprises a plurality of light sources, each light source being incident upon a respective zone of the test strip.

In principle, an assay result reading device in accordance with the present disclosure may comprise any number of light sources and any number of photodetectors. For example, one embodiment includes three light sources, each illuminating a respective zone of a test strip, and a single photodetector which is shared by all three zones. In practice it is difficult to arrange for more than three zones to share a single photodetector, because the photodetector will have trouble in detecting a sufficiently strong signal from those zones which are furthest away.

In preferred embodiments, an assay result reader feature both "shared" photodetectors as well as "commonly read" zones; i.e., a single photodetector can receive light emanating from more than one zone, and light emanating from a single zone is received by more than one photodetector. In this instance, the reader will typically include a plurality of light sources and a smaller plurality of photodetectors. In particular, where the reader comprises x light sources for illuminating the test strip, it will comprise x−1 photodetectors. The number of detectors required might be reduced still further by sharing of the photodetectors between the respective light sources, e.g. using three photodetectors to detect light emanating from an assay test strip that has been illuminated by five light sources.

More specifically, a preferred embodiment of an assay result readers includes first, second and third light sources, each light source illuminating respective first, second or third zones of a test strip. Conveniently the first light source illuminates a test zone or detection zone; the second light source illuminates a reference zone; and the third light source illuminates a control zone. The test or detection zone is a zone of the test strip in which an optical signal is formed (e.g. accumulation or deposition of a label, such as a particulate coloured binding reagent) in the presence or absence, as appropriate, of the analyte of interest. (By way of explanation some assay formats, such as displacement assays, may lead to the formation of signal in the absence of the analyte of interest). The control zone is a zone of the test strip in which an optical signal is formed irrespective of the presence or absence of the analyte of interest to show that the test has been correctly performed and/or that the binding reagents are functional. The reference zone is a zone wherein, typically, only "background" signal is formed which can be used, for example, to calibrate the assay result reading device and/or to provide a background signal against which the test signal may be referenced.

In this particular preferred embodiment, the reader also includes two photodetectors. The first photodetector is substantially adjacent to or primarily associated with the first light source and is intended to detect light emanating the zone of the test strip illuminated by the respective light source. However, the photodetector is so positioned as to be also capable of detecting some of the light emanating from the second zone of the test strip, illuminated by the second light source.

The second photodetector is substantially adjacent to or primarily associated with the third light source and is intended to detect light emanating from the zone of the test strip illuminated by the respective light source. However the photodetector is so positioned as to be also capable of detecting some of the light emanating from the second zone of the test strip, illuminated by the second light source.

Accordingly, this embodiment features a "shared" photodetector, because it includes a plurality of light sources and a photodetector which detects light emanating from at least two spatially separated zones of the test strip. In addition, this embodiment has "commonly read" zones, because it comprises two photodetectors, both of which are able to detect some of the light emanating from a zone of the test strip (in this instance, two photodetectors are able to detect light emanating from the second zone of the test strip).

It is preferred that, when the assay strip is correctly inserted into a reader device, a commonly read zone will be at a position intermediate between the two photodetectors, such that (within certain limits) a lateral movement away from one of the photodetectors will inevitably involve a corresponding lateral movement towards the other photodetectors, so as to allow for the desired signal compensation effect. Typically, but not essentially, the commonly read zone will be approximately equidistant from the two photodetectors when the test strip is correctly positioned within the reader.

It is also preferred that, where an assay result reading device includes a plurality of light sources, these are advantageously arranged such that a particular zone is illuminated only by a single one of the plurality of light sources. For example, optical baffles may be provided between or around the light sources so as to limit the portion of the test strip illuminated by each light source.

For the avoidance of doubt, it is expressly stated that any features described as "preferred", "desirable", "convenient", "advantageous" or the like may be adopted in an embodiment of an assay result reader in combination with any other feature or features so-described, or may be adopted in isolation, unless the context dictates otherwise.

EXAMPLES

A number of Examples are provided to illustrate selected aspects and embodiments of the disclosed subject matter. These Examples merely provide instantiations of systems, devices, and/or methods and are not intended to limit the scope of the disclosure.

Example 1

Figure 1:
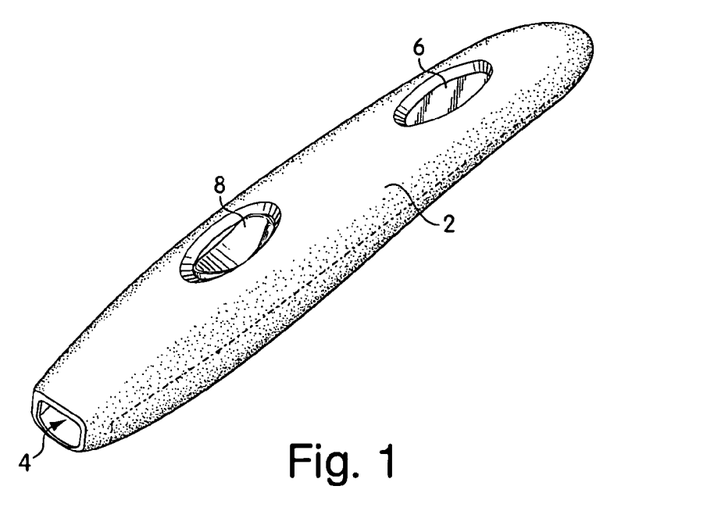
FIG. 1 is a perspective view of an assay result reader.

An embodiment of an assay result reading device having both "shared" photodetectors and "commonly read" zones is illustrated in FIG. 1.

The reading device is about 12 cm long and about 2 cm wide and is generally finger or cigar-shaped. In preferred embodiments, the housing is no larger than about 12 cm long, about 2.5 cm wide, and about 2.2 cm tall. However, any convenient shape may be employed, such as a credit card shaped reader. The device comprises a housing 2 formed from a light-impermeable synthetic plastics material (e.g. polycarbonate, ABS, polystyrene, high density polyethylene, or polypropylene or polystyrol containing an appropriate light-blocking pigment, such as carbon). At one end of the reading device is a narrow slot or aperture 4 by which a test strip (not shown) can be inserted into the reader.

On its upper face the reader has two oval-shaped apertures. One aperture accommodates the screen of a liquid crystal display 6 which displays information to a user e.g. the results of an assay, in qualitative or quantitative terms. The other aperture accommodates an eject mechanism actuator 8 (in the form of a depressible button), which when actuated, forcibly ejects an inserted assay device from the assay reading device.

The test strip for use with the reading device is a generally conventional lateral flow test stick e.g. of the sort disclosed in U.S. Pat. Nos. 6,156,271, 5,504,013, EP 728309, or EP 782707. The test strip and a surface or surfaces of the slot in the reader, into which the test strip is inserted, are so shaped and dimensioned that the test strip can only be successfully inserted into the reader in the appropriate orientation.

When a test strip is correctly inserted into the reader, a switch is closed which activates the reader from a "dormant" mode, which is the normal state adopted by the reader, thereby reducing energy consumption.

Figure 2:
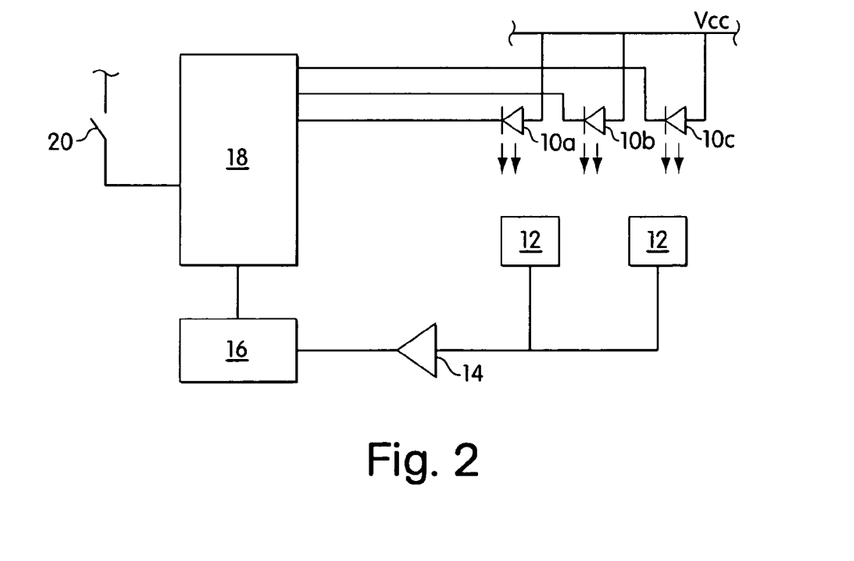
FIG. 2 is a block diagram illustrating schematically some of the internal components of the reading device embodiment depicted in FIG. 1.

Enclosed within the housing of the reader (and therefore not visible in FIG. 1) are a number of further components, illustrated schematically in FIG. 2.

Referring to FIG. 2, the reader comprises three LED's 10a, b, and c. When a test strip is inserted into the reader, each LED 10 is aligned with a respective zone of the test strip. LED 10a is aligned with the test zone, LED 10b is aligned with the reference zone and LED 10c is aligned with the control zone. Two photodiodes 12 detect light reflected from the various zones and generate a current, the magnitude of which is proportional to the amount of light incident upon the photodiodes 12. The current is converted into a voltage, buffered by buffer 14 and fed into an analogue to digital converter (ADC, 16). The resulting digital signal is read by microcontroller 18.

One photodiode detects light reflected from the test zone and some of the light reflected from the reference zone. The other photodiode 12 detects some of the light reflected from the reference zone and the light reflected from the control zone. The microcontroller 18 switches on the LED's 10 one at a time, so that only one of the three zones is illuminated at any given time—in this way the signals generated by light reflected from the respective zones can be discriminated on a temporal basis.

FIG. 2 further shows, schematically, the switch 20 which is closed by insertion of an assay device into the reader, and which activates the microcontroller 18. Although not shown in FIG. 2, the device further comprises a power source (typically a button cell), and an LCD device responsive to output from the microcontroller 18.

In use, a dry test strip (i.e. prior to contacting the sample) is inserted into the reader, this closes the switch 20 activating the reader device, which then performs an initial calibration. The intensity of light output from different LED's 10 is rarely identical. Similarly, the photodetectors 12 are unlikely to have identical sensitivities. Because such variation could affect the assay reading an initial calibration is effected, in which the microcontroller adjusts the length of time that each of the three LED's is illuminated, so that the measured signal from each of the three zones (test, reference and control) is approximately equal and at a suitable operating position in a linear region of the response profile of the system (such that a change in intensity of light reflected from the various zones produces a directly proportional change in signal).

After performing the initial calibration, the device performs a further, finer calibration. This involves taking a measurement ("calibration value") of reflected light intensity for each zone whilst the test strip is dry—subsequent measurements ("test values") are normalised by reference to the calibration value for the respective zones (i.e. normalised value=test value/calibration value).

To conduct an assay, a sample receiving portion of the test strip is contacted with the liquid sample. In this case of a urine sample for instance, the sample receiving portion may be held in a urine stream, or a urine sample collected in a receptacle and the sample receiving portion briefly (about 5–10 seconds) immersed in the sample. Sampling may be performed whilst the test strip is inserted in the reader or, less preferably, the strip can be briefly removed from the reader for sampling and then reintroduced into the reader.

Measurements of reflected light intensity from one or more (preferably all three) of the zones are then commenced, typically after a specific timed interval following insertion of the test strip into the reader. Desirably the measurements are taken at regular intervals (e.g. at between 1–10 second intervals, preferably at between 1–5 second intervals). The measurements are made as a sequence of many readings over short (10 milliseconds or less) periods of time, interleaved zone by zone, thereby minimising any effects due to variation of ambient light intensity which may penetrate into the interior of the reader housing.

Example 2

This example described in greater detail the features of the preferred arrangement of LED's and photodiodes outlined in Example 1.

Figure 3:
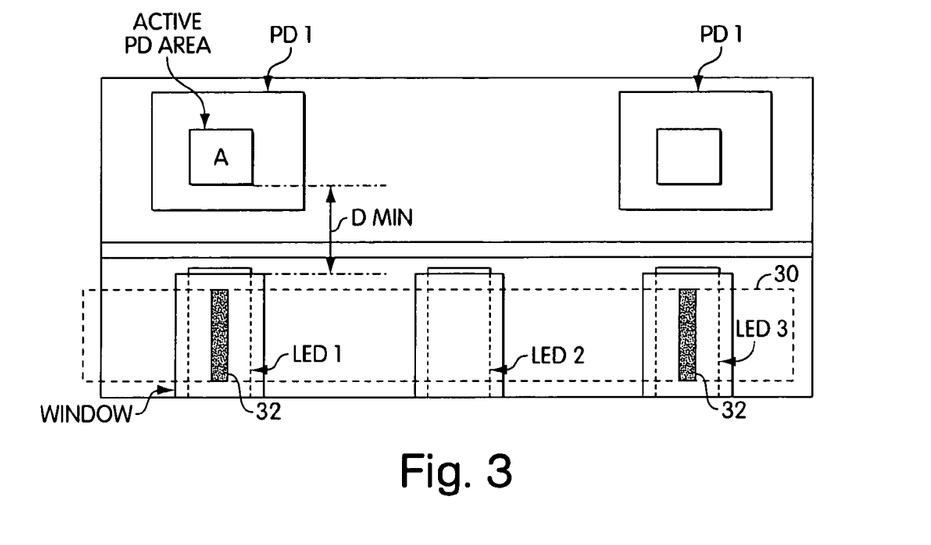
FIG. 3 is a plan view of certain internal components showing an embodiment of one arrangement.

FIG. 3 shows a plan view of an exemplary embodiment of an optical arrangement. In this embodiment, the optical arrangement include three light emitting diodes and two photodetectors. The active area (A) of the photodetectors (PD) is 1.5 mm×1.5 mm. The optics are arranged such that center lines of LED's 1 and 3 correspond to the center lines of PD 1 and PD2. The 3 LED's and two photodetectors are disposed within an area no larger than about 1 square cm, preferably no larger than about 0.7 square cm, specifically 1 cm×0.7 cm.

Also shown is the position of the test-strip 30 that is positioned above the LED's. The test-strip is inserted so that the test and control lines 32 are situated above respectively LED's 1 and 3. The distance D, namely the distance between the PD and LED, is preferably large enough to prevent specular reflection of light emitted from the LED from the surface of the test-strip directly to the PD. This distance will be dependent upon various factors such as the size of the windows, as well as the distance between the windows and the LED's and will be best determined by routine experimentation. The windows are situated above the respective LED's that effectively define the areas through which light shines. In one exemplary embodiment, the dimensions of the window are 2 mm wide by 2.75 mm high.

Figure 4:
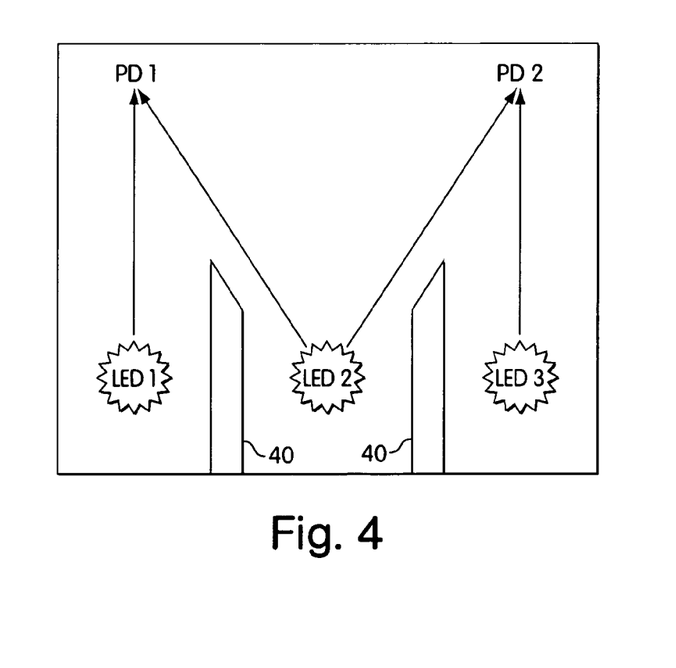
FIG. 4 is a plan view showing an arrangement of certain internal components.

FIG. 4 is a schematic representation of the layout of the 3 LED/2 Photodiode optical system described in Example 1.

FIG. 4 depicts an optics block component for accommodation within an assay result reading device that includes three LED's (LED 1, 2 and 3) and two photodetectors (PD1 and PD2). Light from LED 1 illuminates a test zone of a test strip (not shown) inserted into the reader. Light reflected from the test zone is detected by PD1. Light from LED3 illuminates a control zone of the test strip and light reflected therefrom is detected by PD2. Light from LED2 illuminates a reference zone of the test strip.

Each LED is optically isolated by light-impermeable baffles 40, which ensure that each LED is capable of illuminating only its respective zone of the test strip. However the surfaces of the baffles facing LED2 are angled so as to allow both PD1 and PD2 to collect reflected light from the maximum area of the reference zone.

Figure 5:
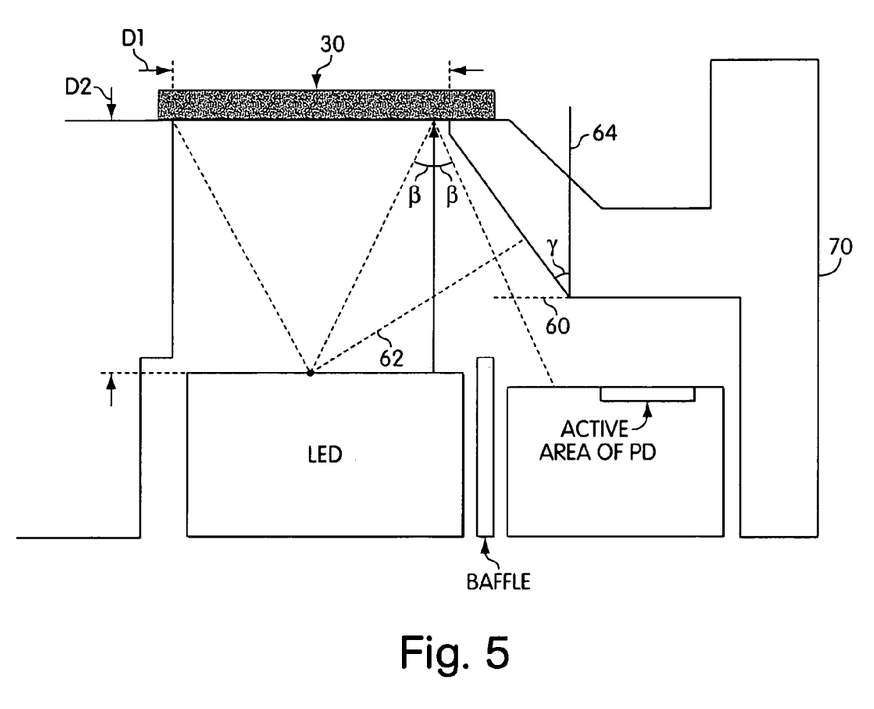
FIG. 5 is an elevation view of certain internal components showing an embodiment of one arrangement and exemplary optical paths.

FIG. 5 shows the spatial relationship between the LED and photodiode. The photodiode is positioned at a sufficient distance to ensure that it does not receive specular reflections from the front cover of the test-strip 30. Specular reflections are a direct reflection. Thus any light hitting the test-strip at an angle β will also reflect at the same angle. Thus to avoid the PD detecting specular light, it is offset. The degree of offset is dependent upon the height D2, the window opening width D1.

The substrate 70 supporting the window is made from black plastic and is chosen to be at a particular angle γ. If the plastic were constructed so as to have a horizontal roof (as denoted dashed line 60), light from the LED could bounce of the roof and onto the PD. To avoid this the substrate is angled such that light hitting the angled part reflects directly back (as denoted by dashed line 62). Again this angle is dependent upon D1 and is approx 40% in the device shown by reference to the solid line 64.

Finally the height of the divide is chosen to be a certain height such that light from the LED does not shine directly to the PD. The height of the divide will be determinant upon the height of the LED. In one exemplary embodiment, the LED height is 1.5 mm and the divide height 2 mm.

In a preferred embodiment the test strip comprises of a layer of a porous carrier such as nitrocellulose sandwiched between two layers of plastic such as MYLAR®. The layer proximal to the light source must be permeable to light, preferably transparent. In the situation wherein the PD's and LED are situated on the same side of the test-strip the layer distal to the light source must be capable of reflecting light. It is preferable for this distal layer to be white to increase contrast and hence the signal to noise ratio.

It is apparent that, in view of the inverse square law, it would generally be preferred to position the photodiodes as close as possible to the test strip (i.e. decrease x), so as to increase the signal intensity I. However, merely decreasing the vertical separation y between the photodiode and the test strip would increase angle θ, decreasing the value of cos θ and therefore tend to reduce the signal intensity.

An alternative approach to improve signal intensity would be to re-position the photodiode nearer the center of the system, which would simultaneously decrease the reflection distance and the angle of reflection. However the distance must be minimized to ensure that the maximum intensity of light is detected (the intensity decreases as a function of the distance of the PD from the test-strip and the angle of reflection).

Example 3

In one exemplary embodiment, the active area of the photodetector is 2 mm×2 mm. The light source provides light, at least some of which has a wavelength of 635 nm.

The height of the test-strip above the light source is 5.5 mm. The wall height separating the LED's is 2.7 mm and the angle of the wall is 30 degrees. The plastic used is black nylon.

Example 4

FIGS. 6–11 illustrate an exemplary embodiment of portions of an assay reader.

Figure 6:
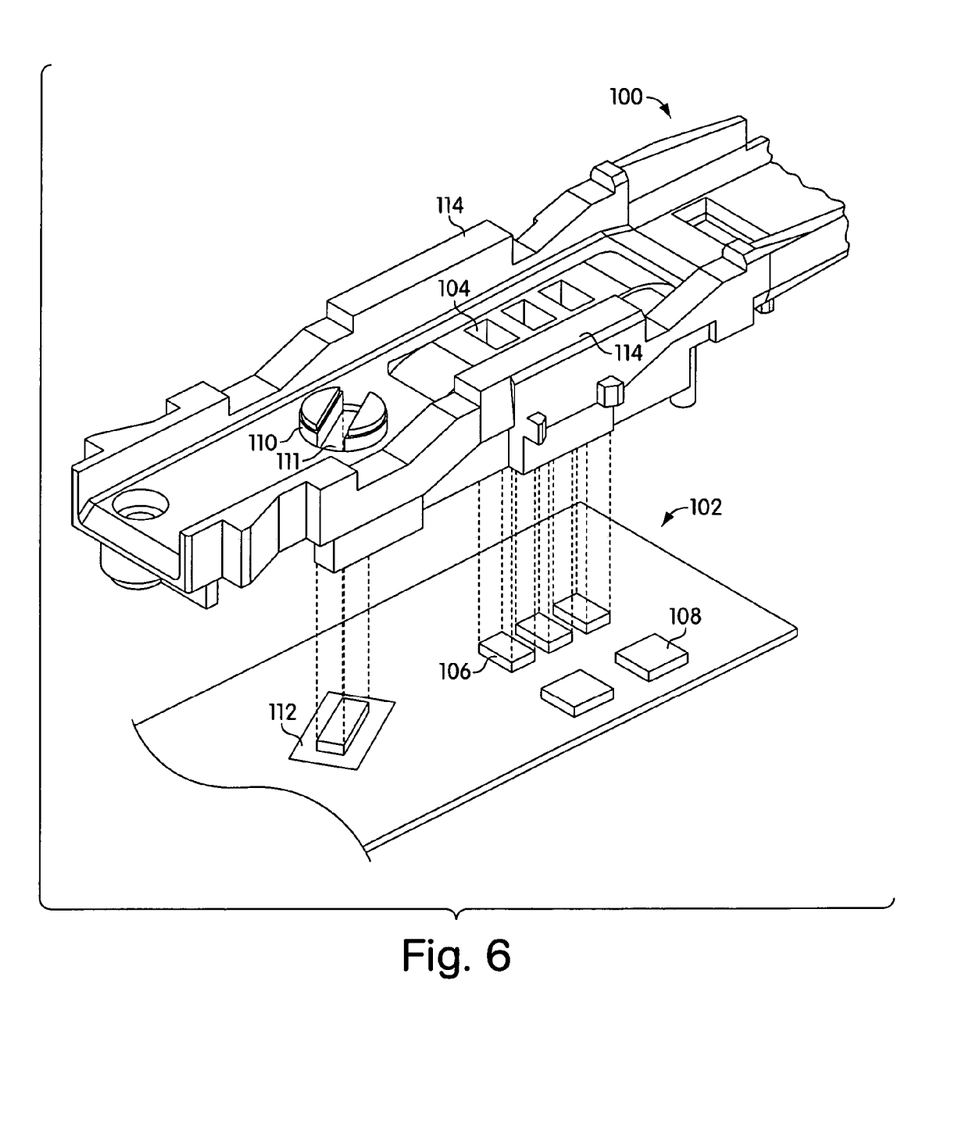
FIG. 6 is an exploded top perspective view of a baffle element and a circuit board of an exemplary embodiment.

FIG. 6 shows an exploded view of a baffle arrangement 100 and a printed circuit board (PCB) 102 that may receive the baffle arrangement. The baffle arrangement defines three windows 104 and includes a location feature 110 which may define an aperture 111 or some other feature that can engage a corresponding feature 112 on the PCB. The location feature 110 may also be so sized and shaped as to engage a mating feature on a test strip (not shown) when the test strip is introduced to the baffle arrangement. The strip may thus be locked into position during an assay measurement. The baffle arrangement also includes parallel raised side walls 114 that may guide the test strip into the correct location and ensure that it both engages with the location feature and is correctly linearly aligned with the windows 104 and not skewed. The PCB includes, among other item not shown, light sources such as light emitting diodes (LED's) 106 and light detectors such as photodiodes (PD's) 108. The LED's and PD's may be mounted in the same plane and positioned under the respective windows 104 such that light emitted from one or more LED's is able to pass through the window spaces onto the test-strip and be reflected back down onto one or more of the PD's.

Figure 7:
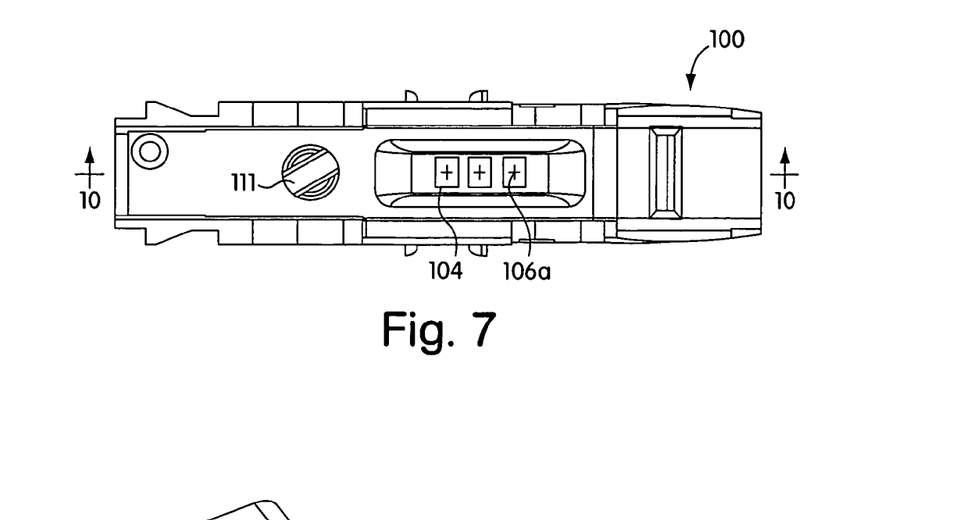
FIG. 7 is a top plan view showing an exemplary baffle arrangement.

FIG. 7 shows a top plan view of an exemplary embodiment of a baffle arrangement 110 in which the light source centers 106a are aligned under their respective windows 104.

Figure 8:
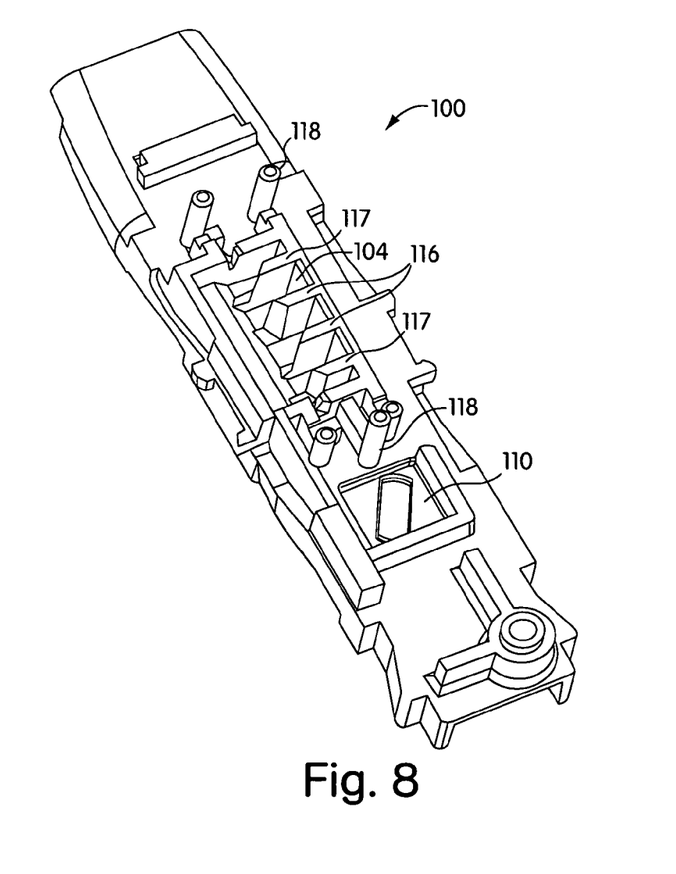
FIG. 8 is a bottom perspective view showing an exemplary baffle arrangement.

FIG. 8 provides an underside view of baffle arrangement 100. The arrangement may include a number of mounting pins 118 to provide contact points with the PCB (not shown). Defining windows 104 are baffles 116 and side barriers 117 that have angled walls to screen light as described above.

Figure 9:
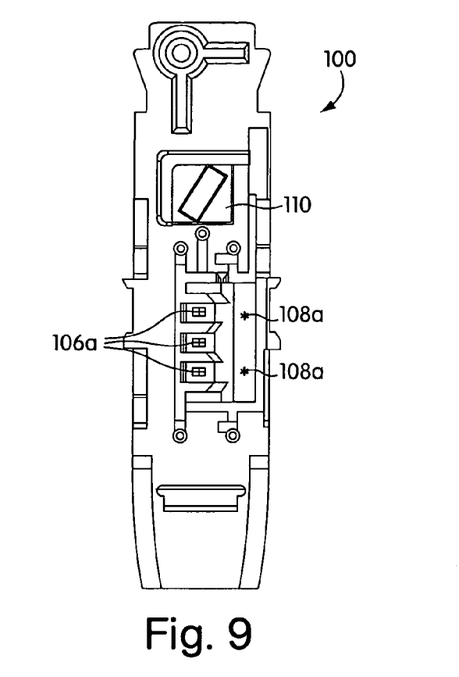
FIG. 9 is a bottom plan view showing an exemplary baffle arrangement.

FIG. 9 shows a bottom plan view of the baffle arrangement 100. The light source centers 106a are aligned under windows 104, and light detector centers 108a are offset to provide the appropriate incident angle, as described above.

Figure 10:
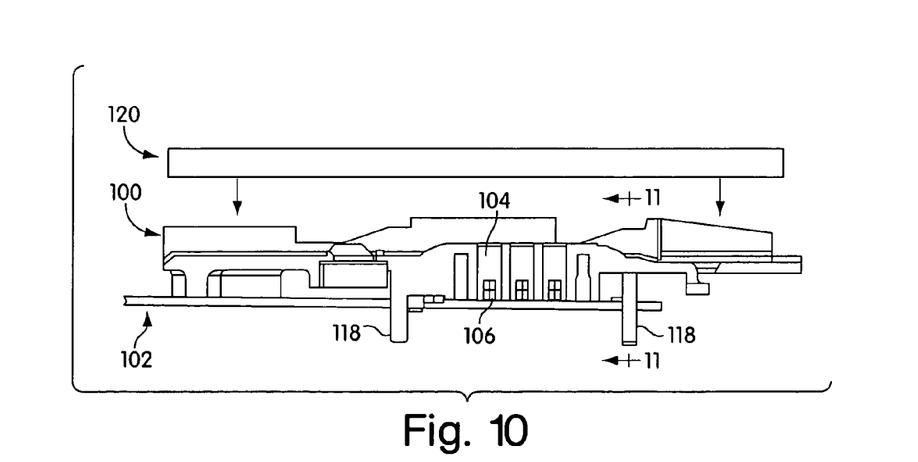
FIG. 10 is an exploded cross-sectional side view taken at line 10—10 in FIG. 7 showing an exemplary baffle arrangement, circuit board, and a test strip.

FIG. 10 depicts a longitudinal cross-section (taken at line 10—10 in FIG. 7) of baffle arrangement 100 seated on PCB 102 and a test strip 120 raised from its normal position in the baffle arrangement. The light sources 106 are positioned in their respective windows 104.

Figure 11:
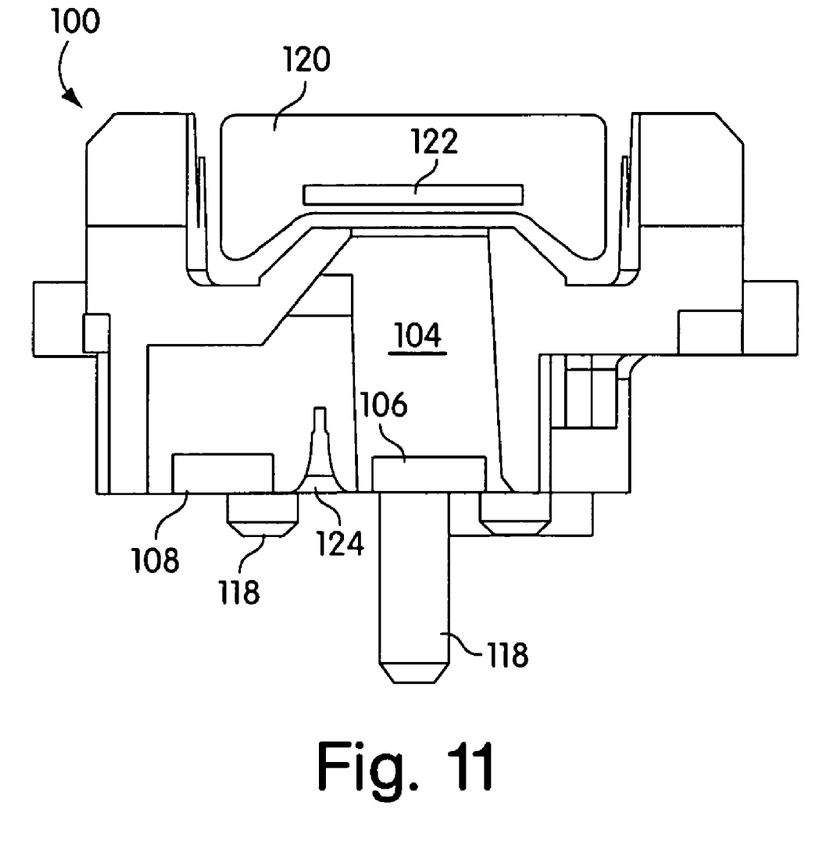
FIG. 11 is a transverse cross-sectional view taken at line 11—11 in FIG. 10 showing an exemplary baffle arrangement and a test strip.

FIG. 11 is a transverse cross section (taken at line 11—11 in FIG. 10) showing the test strip 120 in position relative to the baffle arrangement 100. The strip includes a porous carrier membrane 122 in which the assay reaction is conducted. Light emanative from a light source 106 impinges on the membrane. Light emanating from the membrane is detected by the light detector 108. A divider 124 prevents light from source 106 from shining directly on detector 108.

Example 5

An assay result reader according to the present disclosure may also include a system for declaring the result of an assay before completion of the assay, if a analyte measurement signal is above an upper threshold or below a lower threshold. Such systems are described in U.S. patent application Ser. No. 10/741,416, filed Dec. 19, 2003.

Example 6

An assay result reader according to the present disclosure may also include a system for detecting flow rate of a fluid sample, such as one described in U.S. patent application Ser. No. 10/742,459, filed Dec. 19, 2003.

Example 7

An assay result reader according to the present disclosure may further include both an early declaration system described in U.S. patent application Ser. No. 10/741,416 and a flow rate detection system described in U.S. patent application Ser. No. 10/742,459.

All patents and patent applications mentioned herein are hereby incorporated by reference in their entirety as if each individual patent or application were specifically and individually indicated to be incorporated by reference. In case of conflict, the present application, including any definitions herein, will control.

The invention claimed is:

1. An assay result reading device for reading the result of an assay performed using a test strip, the device comprising:
   at least one light source capable of emitting light incident upon at least first, second, and third spatially separated zones of the test strip, the light source comprising three light emitting diodes (LED's), each of which is aligned with and laterally offset from a corresponding test strip zone;
   a first baffle so sized and positioned as to prevent light emitted by the first LED from illuminating the third zone;
   a second baffle so sized and positioned as to prevent light emitted by the third LED from illuminating the first zone;
   a first photodetector so positioned to detect light emanating from the first zone and the second zone; and
   a second photodetector so positioned as to receive light emanating from the second zone and the third zone.

2. A reading device according to claim 1, wherein the first and second photodetectors are positioned on opposite sides of and laterally offset from one of the zones.

3. A reading device according to claim 1, wherein at least one of the first and second photodetectors comprises a photodiode.

4. A reading device according to claim 1, wherein at least one of the first and second photodetectors is positioned between and laterally offset from two of the zones.

5. A reading device according to claim 1, further comprising a housing enclosing the at least one light source and the first and second photodetectors.

6. A reading device according to claim 5, wherein the housing is about 12 cm long or less, about 2.5 cm wide or less, and about 2.2 cm tall or less.

7. A reading device according to claim 1, wherein the at least one light source and the first and second photodetectors are disposed within an area about 1 square centimeter or less.

8. A reading device according to claim 1, wherein the at least one light source and the first and second photodetectors are disposed within an area about 0.7 square centimeter or less.

9. A reading device according to claim 1, further comprising:
   a computation circuit responsive to signals generated by at least one of the first and second photodetectors representing the presence or absence of a fluid sample in at least one of the zones to:
calculate a flow rate for a fluid flowing along the test strip;
compare the calculated flow rate to upper and lower limits; and
reject the assay result if the calculated flow rate is outside the upper and lower limits.

10. A reading device according to claim 1, further comprising:
a computation circuit, responsive to an input signal representing the amount of an analyte or the rate of accumulation of an analyte in at least one of the zones of the test strip, to:
compare the input signal to a first threshold;
compare the input signal to a second threshold, the second threshold being less than the first threshold;
generate an output signal if the input signal exceeds the first threshold or the input signal is less than the second threshold, the output signal indicative of a first result if the input signal exceeds the first threshold, or, alternatively, the output signal indicative of a second result if the input signal is less than the second threshold; and
terminate the assay if the input signal exceeds the first threshold or the signal is less than the second threshold.

11. A reading device according to claim 10, further comprising:
a computation circuit responsive to signals generated by at least one of the first and second photodetectors representing the presence or absence of a fluid sample in at least one of the zones to:
calculate a flow rate for a fluid flowing along the test strip;
compare the calculated flow rate to upper and lower limits; and
reject the assay result if the calculated flow rate is outside the upper and lower limits.

12. An assay result reading device for reading the result of an assay performed using a test strip, the device comprising:
at least one light source capable of emitting light incident upon at least first, second, and third zones of the test strip; and
at least two photodetectors, the first of which detects light emanating from the first zone and second zone of the test strip; and the second of which detects light emanating from the second zone and the third zone of the test strip.

13. A method of determining a result of an assay performed using a test strip, the method comprising:
positioning a test strip, having first, second, and third spatially separated zones, in relation to an assay result reader, the reader comprising a housing enclosing at least at least three light sources and two photodetectors; and
measuring at least one light level received by at least one photodetector; and determining, using a processor and based on the at least one light level, the result of the assay performed on the test strip; and
displaying a value indicative of the result of the assay; wherein:
each light source is aligned with and laterally offset from a corresponding test strip zone;
the first photodetector is so positioned as to receive light emanating from the first zone and the second zone; and
the second photodetector is so positioned as to receive light emanating from the second zone and the third zone.

14. A method according to claim 13, wherein the test strip is positioned at least partly inside the assay result reader.

15. An assay result reading device for reading the result of an assay performed using a test strip, the device comprising:
at least one light source system configured to illuminate at least two spatially separated zones of the test strip;
a photodetector system configured to detect light emanating from each of the two said zones; and
a computation circuit responsive to signals generated by the photodetector representing the presence or absence of a fluid sample in at least one of the zones to:
calculate a flow rate for a fluid flowing along the test strip;
compare the calculated flow rate to upper and lower limits; and
reject the assay result if the calculated flow rate is outside the upper and lower limits.

16. The device of claim 15, wherein the light source system comprises a light emitting diode configured to illuminate at least two spatially separated zones of the test strip.

17. The device of claim 15, wherein the photodetector system comprises a photodiode configured to detect light emanating from each of the two zones.

18. An assay result reading device for reading the result of an assay performed using a test strip, the device comprising:
at least one light source system configured to illuminate at least two spatially separated zones of the test strip;
a photodetector system configured to detect light emanating from each of the two said zones; and
a computation circuit, responsive to an input signal representing the amount of an analyte or the rate of accumulation of an analyte in at least one of the zones of the test strip, to:
compare the input signal to a first threshold;
compare the input signal to a second threshold, the second threshold being less than the first threshold;
generate a first output signal if the input signal exceeds the first threshold or a second output signal if the input signal is less than the second threshold.

19. The device of claim 18, wherein the light source system comprises a light emitting diode configured to illuminate at least two spatially separated zones of the test strip.

20. The device of claim 18, wherein the photodetector system comprises a photodiode configured to detect light emanating from each of the two zones.

21. The device of claim 18, wherein the computation circuit indicates that an assay is void if the input signal exceeds the first threshold or is less than the second threshold.

22. A device, comprising:
a housing configured to retain a test strip in a test position;
a light source system configured to illuminate selectively first, second, and third different zones of a test strip retained in the test position;
a first light detector configured to (a) detect light from the first zone of a test strip retained in the test position when the light source illuminates the first zone, and (b)

detect light from the second zone of a test strip retained in the test position when the light source illuminates the second zone;

a second light detector configured to (a) detect light from the third zone of a test strip retained in the test position when the light source illuminates the third zone, and (b) detect light from the second zone of a test strip retained in the test position when the light source illuminates the second zone; and a processor configured to receive respective signals indicative of light detected by the first and second light detectors.

23. The device of claim 22, wherein the housing is configured so that a liquid sample can be applied to a test strip retained in the test position.

24. The device of claim 23, further comprising a test strip retained in the test position.

25. The device of claim 24, wherein the housing completely encloses the first, second, and third zones of the test strip.

26. The device of claim 24, wherein the test strip comprises a lateral flow away test strip.

27. The device of claim 26, wherein the test strip is configured to allow the liquid sample to flow along the test strip between at least two of the first, second, and third zones, and the processor is configured to determine a flow rate of the liquid based on signals received from at least one of the first and second light detectors.

28. The device of claim 27, wherein the processor is configured to determine the flow rate of the liquid based on signals received from both the first and second light detectors.

29. The device of claim 27, wherein the processor is configured to determine the presence of an analyte based on signals received from at least one of the first and second light detectors.

30. A method, comprising:
allowing a liquid to advance along a test strip after having been applied thereto;
illuminating a first zone of the test strip with light from a first light source;
detecting light from the illuminated first zone using a first light detector;
illuminating a second zone of the test strip with light from a second light source;
detecting light from the illuminated second zone using the first light detector;
detecting light from the illuminated second zone using a second light detector;
illuminating a third zone of a test strip with light from a third light source;
detecting light from the illuminated third zone using the second light detector;
receiving, with a processor, respective signals from the first and second light detectors, the signals indicative of the detected light;
determining, with the processor, a value indicative of a rate at which the liquid advances along the test strip based on the received signals; and
performing at least one action based on the determined value.

31. The method of claim 30, further comprising determining, before performing the at least one action the presence in the liquid of an analyte based at least in part on light detected by the first and second light detectors.

32. The method of claim 30, wherein illuminating the second zone comprises illuminating the second zone at least twice and detecting light from the illuminated second zone using the first detector is performed at a different time from detecting light from the illuminated second zone using the second detector.

33. A device, comprising:
a housing;
a lateral flow test strip disposed in a test position with respect to the housing, the test strip comprising a sample receiving portion extending from the housing and first, second, and third zones disposed within the housing, the test strip defining a flow path along which liquid received by the sample receiving portion can sequentially flow to the first, second, and third zones of the test strip;
a light source system configured to illuminate selectively the first, second, and third zones of the test strip;
a first light detector configured to:
detect light from the first zone of the test strip when the light source illuminates the first zone;
output first signals indicative of light detected from the first zone;
detect light from the second zone of the test strip when the light source illuminates the second zone; and
output second signals indicative of light detected from the second zone;
a second light detector configured to:
detect light from the third zone of a test strip when the light source illuminates the third zone;
output third signals indicative of light detected from the third zone;
detect light from the second zone of a test strip when the light source illuminates the second zone; and
output fourth signals indicative of light detected from the second zone, and a processor configured to receive first and second signals from the first detector and to receive third and fourth signals from the second detector and to determine the presence of an analyte in liquid received by the sample receiving member based at least in part upon the received first, second, third, and fourth signals.

34. The device of claim 33, wherein the processor is configured to determine a time for liquid to flow along the test strip between the first and second zones based upon first and second signals received from the first detector and third and fourth signals received from the second detector.

* * * * *